(12) United States Patent
Hoffmeier et al.

(10) Patent No.: US 11,504,257 B2
(45) Date of Patent: *Nov. 22, 2022

(54) ADJUSTABLE DORSAL NIGHT SPLINT

(71) Applicant: DJO, LLC, Vista, CA (US)

(72) Inventors: Carl Hoffmeier, Solana Beach, CA (US); Tracy Ng, Denver, CO (US); Eileen Zirpolo-Kisco, San Marcos, CA (US)

(73) Assignee: DJO, LLC, Carlsbad, CA (US)

( * ) Notice: Subject to any disclaimer, the term of this patent is extended or adjusted under 35 U.S.C. 154(b) by 420 days.

This patent is subject to a terminal disclaimer.

(21) Appl. No.: 16/565,156

(22) Filed: Sep. 9, 2019

(65) Prior Publication Data

US 2020/0000618 A1 Jan. 2, 2020

Related U.S. Application Data

(63) Continuation of application No. 15/223,468, filed on Jul. 29, 2016, now Pat. No. 10,406,013, which is a continuation of application No. 13/631,424, filed on Sep. 28, 2012, now abandoned, which is a continuation of application No. 12/879,818, filed on Sep. 10, 2010, now Pat. No. 8,409,123.

(51) Int. Cl.
| | | |
|---|---|---|
| *A61F 5/01* | (2006.01) | |
| *A61F 5/058* | (2006.01) | |
| *A61F 5/58* | (2006.01) | |
| *A61H 1/02* | (2006.01) | |
| *A61F 5/30* | (2006.01) | |

(52) U.S. Cl.
CPC .......... *A61F 5/0113* (2013.01); *A61F 5/0585* (2013.01); *A61F 5/30* (2013.01); *A61F 5/58* (2013.01); *A61H 1/0266* (2013.01)

(58) Field of Classification Search
CPC .... A61F 5/0111; A61F 5/0113; A61F 5/0195; A61F 5/01; A61F 5/058; A61F 5/0585; A61F 5/30; A61H 1/0266
USPC .................. 128/846, 882; 602/5, 23, 28, 62; D24/192
See application file for complete search history.

(56) References Cited

U.S. PATENT DOCUMENTS

| | | |
|---|---|---|
| 3,527,209 A | 9/1970 | Baker |
| 5,372,576 A | 12/1994 | Hicks |
| (Continued) | | |

FOREIGN PATENT DOCUMENTS

| | | |
|---|---|---|
| CN | 101711141 B | 4/2013 |
| EP | 2613745 A1 | 7/2013 |
| (Continued) | | |

OTHER PUBLICATIONS

International Search Report filed in PCT/US2011/051050 dated Dec. 5, 2011.

*Primary Examiner* — Caitlin A Carreiro
(74) *Attorney, Agent, or Firm* — Veros Legal Solutions, LLP (57) ABSTRACT

A dorsal night splint has dynamic adjustable features that allow the patient to adjust the splint while in use to control the stretching of the plantar fascia and Achilles. A semi-rigid flexible frame is included along with a tightening strap that is anchored to the frame and by which the patient can tension the strap and adjust the structure of the frame to fit the patient's desired therapeutic or prophylactic needs.

17 Claims, 11 Drawing Sheets

(56) References Cited

U.S. PATENT DOCUMENTS

| | | | |
|---|---|---|---|
| 5,399,155 A | 3/1995 | Strassburg et al. | |
| 5,676,642 A | 10/1997 | Peters | |
| 5,700,237 A | 12/1997 | Hess | |
| 5,776,090 A | 7/1998 | Bergmann et al. | |
| 5,799,659 A | 9/1998 | Stano | |
| 6,019,741 A | 2/2000 | Prieskorn | |
| 6,131,311 A | 10/2000 | Brown et al. | |
| 6,267,742 B1 | 7/2001 | Krivosha et al. | |
| 6,350,246 B1 | 2/2002 | DeToro et al. | |
| 7,115,105 B2 | 10/2006 | Cropper | |
| 7,179,206 B2 | 2/2007 | Backes et al. | |
| 7,266,910 B2 | 9/2007 | Ingimundarson | |
| D576,781 S | 9/2008 | Chang et al. | |
| D592,756 S | 5/2009 | Chang et al. | |
| 7,597,674 B2 | 10/2009 | Hu et al. | |
| 7,682,325 B2 | 3/2010 | Chan | |
| 7,727,174 B2 | 6/2010 | Chang et al. | |
| 7,749,183 B2 | 7/2010 | Ingimundarson et al. | |
| 8,409,123 B2* | 4/2013 | Hoffmeier | A61F 5/58 602/61 |
| 10,406,013 B2* | 9/2019 | Hoffmeier | A61F 5/58 |
| 2002/0133109 A1 | 9/2002 | Brown | |
| 2007/0167893 A1 | 7/2007 | Frisbie | |
| 2008/0004558 A1 | 1/2008 | Outred et al. | |
| 2008/0072455 A1 | 3/2008 | Svae | |
| 2008/0208094 A1 | 8/2008 | Gaylord | |
| 2008/0294082 A1* | 11/2008 | Chang | A61F 5/0111 602/23 |
| 2009/0264803 A1 | 10/2009 | Darby et al. | |
| 2009/0282699 A1 | 11/2009 | Labogin | |
| 2009/0306566 A1 | 12/2009 | Chan | |
| 2010/0242310 A1 | 9/2010 | Gourineni | |
| 2010/0324461 A1 | 12/2010 | Darby et al. | |
| 2011/0023324 A1 | 2/2011 | Dananberg | |
| 2012/0034048 A1 | 2/2012 | Karupaya | |

FOREIGN PATENT DOCUMENTS

| | | |
|---|---|---|
| FR | 2938184 B1 | 6/2011 |
| WO | 2006010213 A1 | 2/2006 |

\* cited by examiner

ADJUSTABLE DORSAL NIGHT SPLINT

CROSS-REFERENCE TO RELATED APPLICATIONS

This application is a continuation of U.S. patent application Ser. No. 15/233,468, filed on Jul. 29, 2016, which is a continuation of U.S. patent application Ser. No. 13/631,424, filed Sep. 28, 2012, which is a continuation of U.S. patent application Ser. No. 12/879,818, filed Sep. 10, 2010, now issued as U.S. Pat. No. 8,409,123. The contents of each of the aforementioned patent applications are hereby incorporated by reference herein in their entireties.

BACKGROUND OF THE INVENTION

Field of the Invention

Plantar fasciitis is a painful condition that arises when the plantar fascia under a patient's arch become strained or over-stretched. The condition can be particularly painful after extended rest periods during which the fascia stiffen and tighten. When the patient stands after that rest period, the stiffened fascia are pressed by the force of the patient's weight, causing further pain.

Various devices have been used to treat this condition, typically employing a stiff frontal frame that fits against the front of the patient's leg and extends in an L-shape along the patient's forefoot, being held to the patient by straps that wrap around the patient's leg and foot. An example is the dorsal night splint disclosed in U.S. Pat. No. 5,776,090 to Bergman. The Bergman splint includes a frame held to the anterior side of a patient's lower leg by straps. The frame has stiffening ribs that permit it to hold its shape and is bent, prior to the patient putting it on, so the frame's forefoot and foreleg portions are held at a pre-set angle.

A variation in the Bergman splint is disclosed in U.S. Patent Application Publication No. 2008/0208094 of Gaylord. The Gaylord splint has an adjustable stabilizing frame that is also pre-bent to a predetermined angle, and a soft sheet of fabric with tensioning arms that wrap around the perimeter of the leg and frame to anchor the frame to the lower leg. Another example is the Exoform® Dorsal Night Splint sold by Ossur. That splint includes a soft attachment system and a metal plate within a plastic housing. The splint is bent by the patient into a pre-set L-shaped form, prior to application, with the splint retaining this pre-set angle during use. Another variation is disclosed in U.S. Pat. No. 7,682,325 to Chan, which includes a plate that has an accordion-like middle section and is bent into a pre-defined shape.

The frames used in the foregoing products and other similar technologies are cumbersome and are adjustable by the patent only before the frames are applied to the leg. If the splint does not fit properly, it must be removed before it can be adjusted, which takes more time and can lead to reduced patient compliance.

Some technologies have attempted to provide more adjustability to the device. One example is disclosed in U.S. Patent Application Publication No. 2009/0264803 of Darby et al., which includes a flexible frame with a toe strap used to elevate the patient's toes to relieve pain in the plantar fascia. That structure provides no ability for the patient to adjust the frame while positioned on the foot, and thus may not provide for a sufficiently deep stretch of the plantar fascia.

An improved system is needed to address these and other deficiencies, to achieve better fitting splints that can improve patient therapy and produce greater patient compliance.

SUMMARY

Disclosed herein is a contoured, padded splint to be applied to the foot and lower leg of a patient for treatment of plantar fasciitis and Achilles tendinitis. The splint is formed as a brace that is dynamic and adjustable by the patient, after being placed on the patient, allowing the patient to achieve tailored flexion and optimal comfort for addressing these conditions. Patients can sleep at night and start their day with fascia that have been stretched and prepared for walking.

The splint generally includes a semi-rigid flexible frame configured to be applied along the ventral (or anterior) side of the foot and lower leg, and a tightening strap configured to allow the patient to tighten the splint to stretch the plantar fascia.

In certain implementations, the splint includes a semi-rigid flexible frame with a top side and an under side, the frame forming a proximal surface that extends vertically along a user's shin and upper ankle, and a distal surface that extends along the top of the user's foot. The proximal surface has a first receptacle, positioned centrally along the face, for engaging a tightening strap, and the distal surface has a second receptacle for also engaging a tightening strap.

The tightening strap is an inelastic adjustable strap that engages the first and second receptacles and is configured to be tightened by hand after the splint is placed on the patient's lower leg. The tightening strap can be formed in a pulley system, with an extending end. The patient tightens the strap by pulling on the extending end and, as the extended end is pulled, the proximal surface and distal surface are pulled toward each other, thereby stretching the user's plantar fascia under the arch and heel. The proximal and distal surfaces of the frame are then anchored in a fixed position relative to each other by securing the tightening strap.

A soft housing is also included to fit under the user's foot and attach the frame to the user's lower leg. In certain embodiments, the soft housing is made of laminate, Neoprene or other fabric.

In certain implementations, the splint includes a forefoot support pad positioned between the user's toes and the soft housing. The forefoot support pad is configured to fit comfortably to the patient's toes and the ball of the foot. In certain examples, the forefoot support pad includes a distal lift area that fits under the toes, a proximal support area that fits behind the ball of the patient's foot, and a trough between the support areas which holds the ball of the patient's foot.

In certain examples, an adjustable toe strap is included to attach to the soft housing and extend around the distal end of the patient's toes and connect with the distal surface of the frame. In certain examples, the toe strap is configured with an attachment mechanism, such as a D-ring, that allows it to inter-fit with the attachment strap and be secured to the frame by operation and tightening of the attachment strap. In certain examples, a liner or support pad is also used to fit between the frame and the patient's leg, thereby providing comfort and enhanced wearability. In certain implementations, the support pad is made of open cell foam to provide air circulation and moisture wicking.

The frame of the splint may be configured with receptacles, including slots, and hinge mechanisms that receive tightening straps and serve as anchoring points for securing the splint to the patient. In certain examples, the frame includes one or more hinged flaps that extend along lateral and medial edges of the frame, and each flap has a through-hole or slot that receives tightening straps to help adjust and fit the splint to the patient. The frame may also include tapered or cut-out sections that allow the frame to contour to particular anatomical locations on the patient, such as the ankle region.

Various alternative embodiments and sub-features are also disclosed herein with respect to the splint, as will become apparent in the following description.

BRIEF DESCRIPTION OF THE DRAWINGS

Exemplary implementations of the dorsal night splint are described and shown below in the following figures, where like numerals represent like structures in repeating figures.

DETAILED DESCRIPTION OF CERTAIN INVENTIVE EMBODIMENTS

Disclosed herein is a contoured, padded splint to be applied to the lower leg of a patient for treatment of plantar fasciitis and Achilles tendinitis. The splint is dynamic and adjustable by the patient, allowing the patient to achieve tailored flexion and optimal comfort for addressing these conditions. Wearing the splint allows patients to sleep comfortably at night and start their day on a better foot.

The splint includes a semi-rigid flexible frame configured to fit along the ventral (anterior) side of the foot and lower leg, and an inelastic tightening strap configured to allow the patient to tighten the splint and stretch the plantar fascia.

Figure 1:
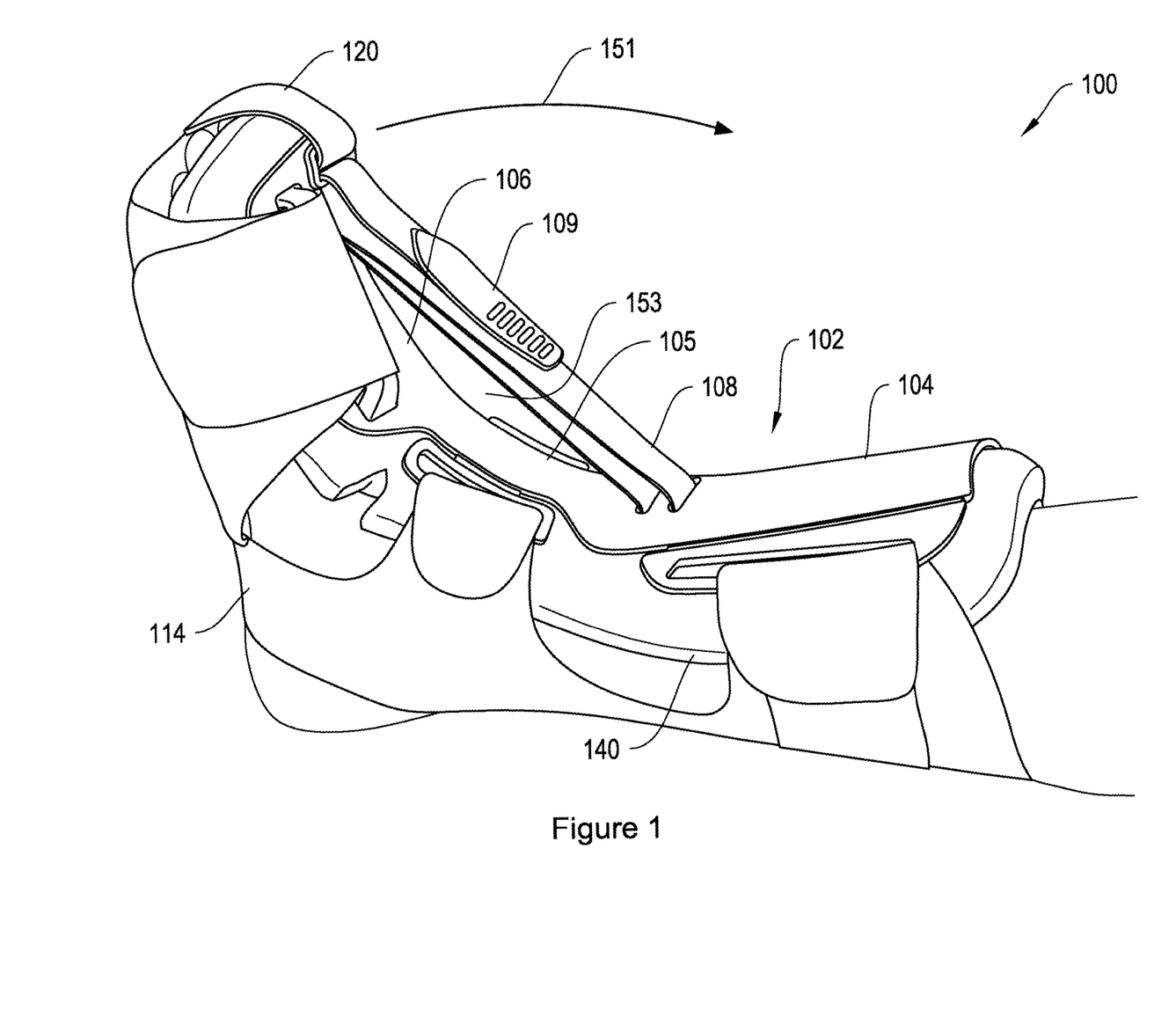
FIG. 1 depicts an exemplary embodiment of a dorsal night splint, applied to a patient's lower leg.

An exemplary embodiment of the splint is shown in FIG. 1 as the splint 100. The splint 100 has a flexible, semi-rigid frame 102 that is applied to a user's lower leg by a flexible soft housing 114 that wraps around the dorsal (posterior) side of the foot and anchors the frame 102 to the leg. As shown, the frame 102 fits over a support pad 140 that cushions the frame 102 against the leg. The pad fits between the patient and the frame 102 and cushions the patient's leg with respect to the frame 102. In certain implementations, the support pad 140 is made of a layer of open-cell foam affixed to a closed-cell foam liner, the closed cell foam liner having hook-and-loop material that attaches to complementary hook-and-loop material on the under side of the frame 102. The open cell foam of the pad 140 provides for air circulation to cool the patient and moderate moisture within the brace, thus improving its usability for nighttime wear. A flexible strap 120 is also included, extending from the distal surface 106, in front of the patient's foot, over the distal tip of the pad 140 and connecting to the splint on the bottom side of the soft housing 114.

The frame 102 includes a proximal surface 104 that fits along the user's lower leg, a distal surface 106 that fits along the user's foot, and a bend 105 that spans between the proximal and distal surfaces. A tightening strap 108 with pull tab 109 extends between the proximal surface 104 and the distal surface 106 of the frame 102, allowing the patient to adjust and tighten the splint by hand while it is applied to the patient's leg, as explained more fully below. The frame 102 is constructed of a semi-rigid but flexible material, which can bend upon the application of a force applied by a tensioning strap but is also sturdy enough to resist that force in a controlled manner, unlike a cloth or sock which would simply fold or stretch when the force is applied. In certain implementations, the frame is made of flexible polypropylene by injection molding, but lightweight aluminum or other semi-rigid materials could also be used.

Figure 2A:
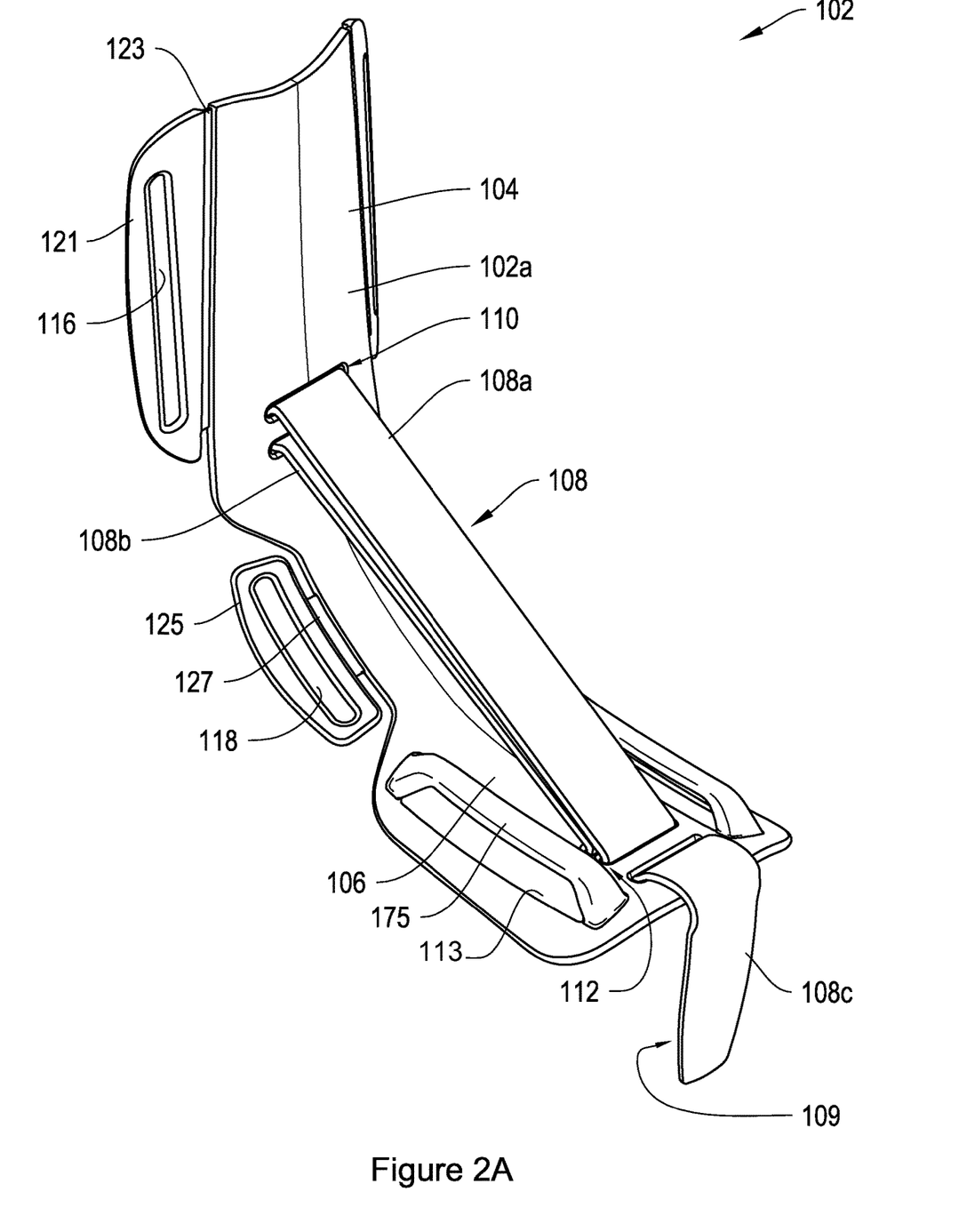
FIGS. 2A and 2B show top and under side views, respectively, of the frame used in an exemplary dorsal night splint according to the disclosure herein.
Figure 2B:
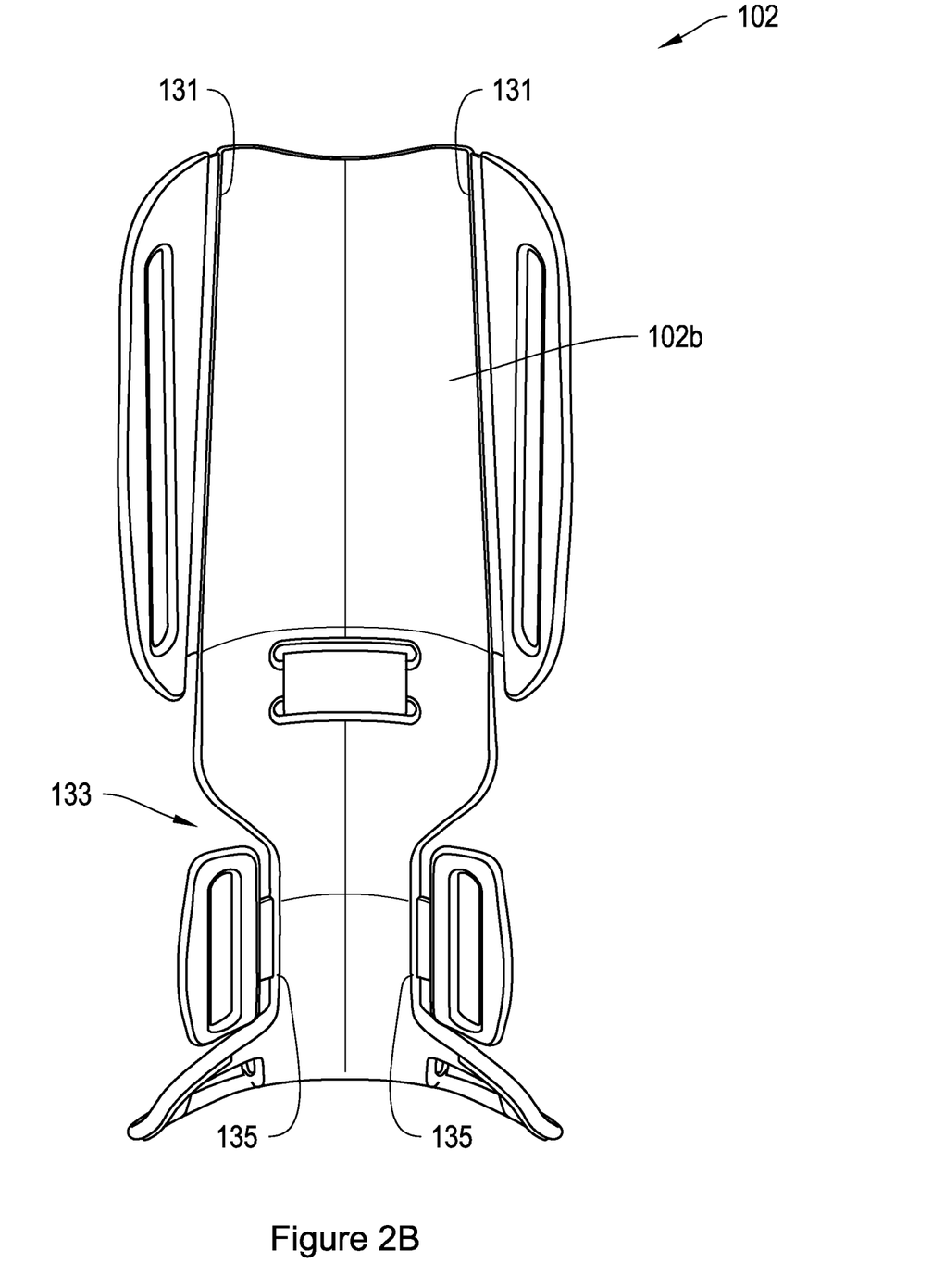

FIGS. 2A and 2B illustrate the frame 102 and its cross strap 108 in further detail. As shown in FIGS. 2A and 2B, the frame 102 has a plurality of hinged flaps 121 and 125 and slots 116 and 118 positioned along respective edges of the frame. In certain embodiments, the hinged flaps and slots are co-molded with the frame and integral to the polypropylene material of the frame. As shown, the flap 121 is connected to the edge 131 of the frame by a thin piece of plastic 123, which because of its thin cross section can bend as a hinge point. Similarly, the flap 125 is connected to the edge 135 of the frame by a thin plastic hinge section 127. The edge 135 forms a cut-out or narrowing section of the frame, providing the carve-out section 133 of bend area 105 that tapers in toward the center of the frame, for a more particular and comfortable fit around the user's ankle. The slot 113 is formed along the edge of the distal surface of the frame by a raised ridge 175 that extends above the distal surface of the frame. Similar structures are also included on the opposite side of the splint. As explained below, the hinged flaps and slots receive straps from the soft housing 114 to help secure the frame 102 to the leg.

The frame also has receptacles 110 and 112, located centrally across the top side of the frame, for engaging the tightening strap 108. The tightening strap 108 is made of nylon or other inelastic material and is folded into a plurality of sections that loop through the receptacles and fold back upon each other, forming a pulley and anchoring system. As shown in FIG. 1, the strap 108 extends directly between the proximal surface 104 and the distal surface 106, bypassing the bend 105, which creates a large space 153 between the strap 108 and the bend 105 along the upper surface 102 a of the frame. The spacing and anchoring, and the inelasticity of the strap, allow the patient to secure and tighten the frame by hand while wearing it, thereby adjusting the tension on the plantar fascia and Achilles.

More particularly, as shown in FIGS. 3A-3B and 4A-4B, the strap 108 has a top section 108a, a bottom section 108b, a distal end section 108c, a proximal end section 108d and a section 108e. The receptacle 112 includes three slots 112a, 112b, and 112c, and the receptacle 110 includes slots 110a and 110b. The proximal end section 108d of the strap 108 is riveted to the under side 102b of the distal surface 106 of the frame 102, creating an anchor point at the rivet 114, and the strap 108 extends through slot 112a at the bottom section 108b. The bottom section 108b extends above the exterior of the frame 102 toward the proximal surface of the frame 102, spaced above the top side 102a (and the bend 105), and protrudes into the slot 110b, forming a fold that loops underneath the proximal surface 104 and then back through the slot 110a. The top portion 108a of the strap extends back across the exterior face of the frame, toward the distal surface of the frame, and into the slot 112b. After passing through slot 112b, the section 108e of the strap 108 forms another fold that passes under the under side 102b of the distal portion of the frame 102 and extends through the slot 112c. After passing through the slot 112c, the strap section 108c extends out the front of the brace where it is received by the patient for tightening. As shown, the pull tab 109 is positioned on one side (or may surround) the distal tip of the strap section 108c.

To tighten the brace, the patient pulls the tab 109 toward him or herself, which pulls the section 108c and in turn pulls the section 108a and then the section 108b. Because of the anchoring of the section 108d against the rivet 114, pulling the strap tightens and lifts the distal surface 106 toward the proximal surface 104, as illustrated by the directional arrow 151 of FIG. 1, thereby lifting the patient's forefoot toward the shin to stretch the fascia tissue on the underside of the foot. The distal surface is drawn toward the proximal surface until the two surfaces reach a desired relative position, whereupon the patent attaches the pull tab 109 to the remainder of the strap 108 (e.g., by Velcro or other hook-and-loop attachment) to anchor the strap and the two surfaces in that position. As shown, the tab 109 is secured to the surface 108a of the strap at a position located between the receptacles 110 and 112 (e.g., a mid-way point), which centers the force applied by the distal and proximal surfaces of the frame between the two receptacles. The two surfaces are thereby anchored in the relative position, having a fixed angle between them which angle can be adjusted by the user while wearing the splint. The tensioning strap 108 thus allows the patient to easily adjust the structure of the frame itself to a desired position and tension while in use. The user can thereby select and apply a constant stretching force to the plantar fascia.

Figure 3A:
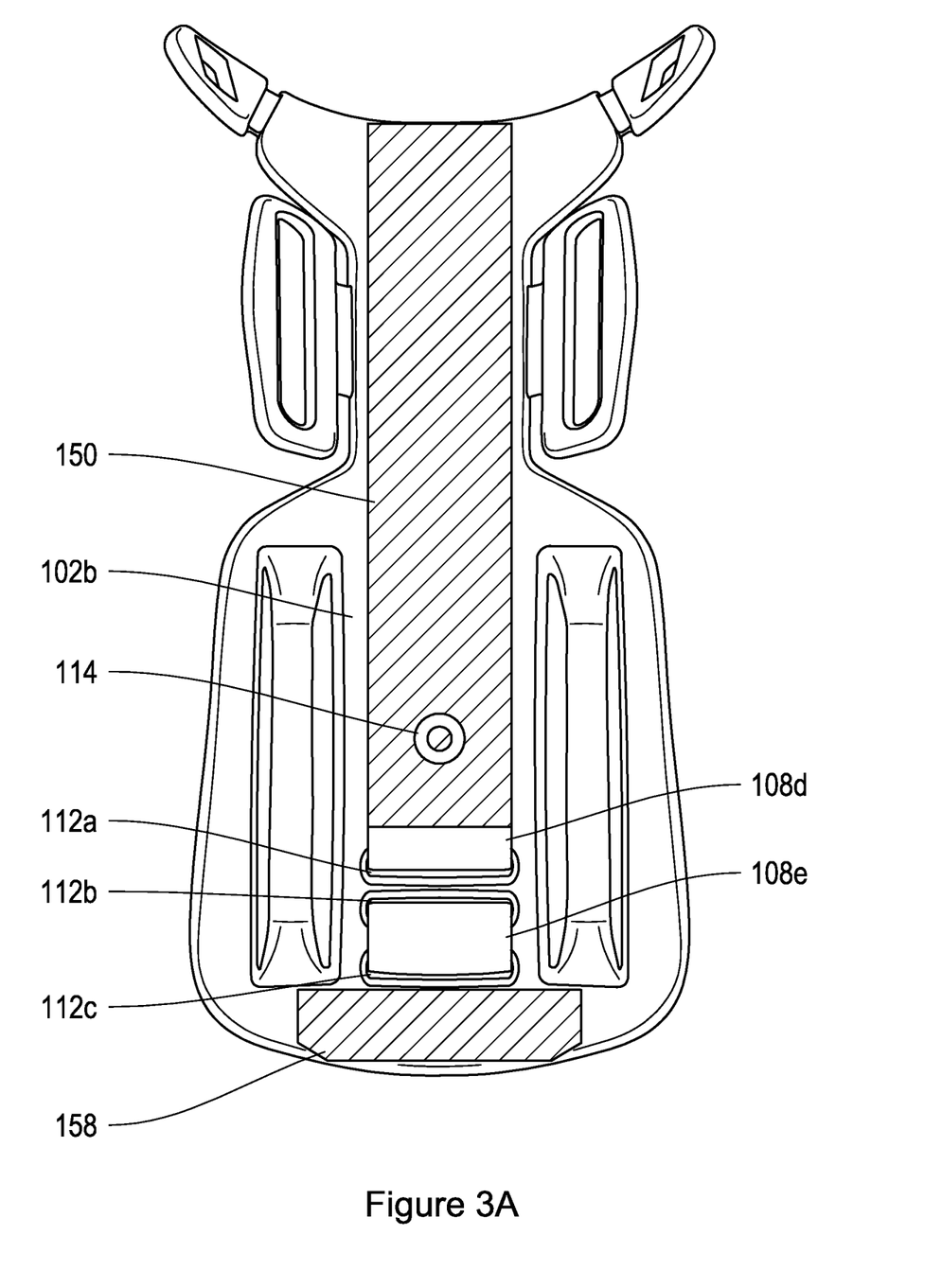
FIGS. 3A and 3B show underside views of the frame of FIGS. 2A and 2B, with an attachment mechanism.
Figure 3B:
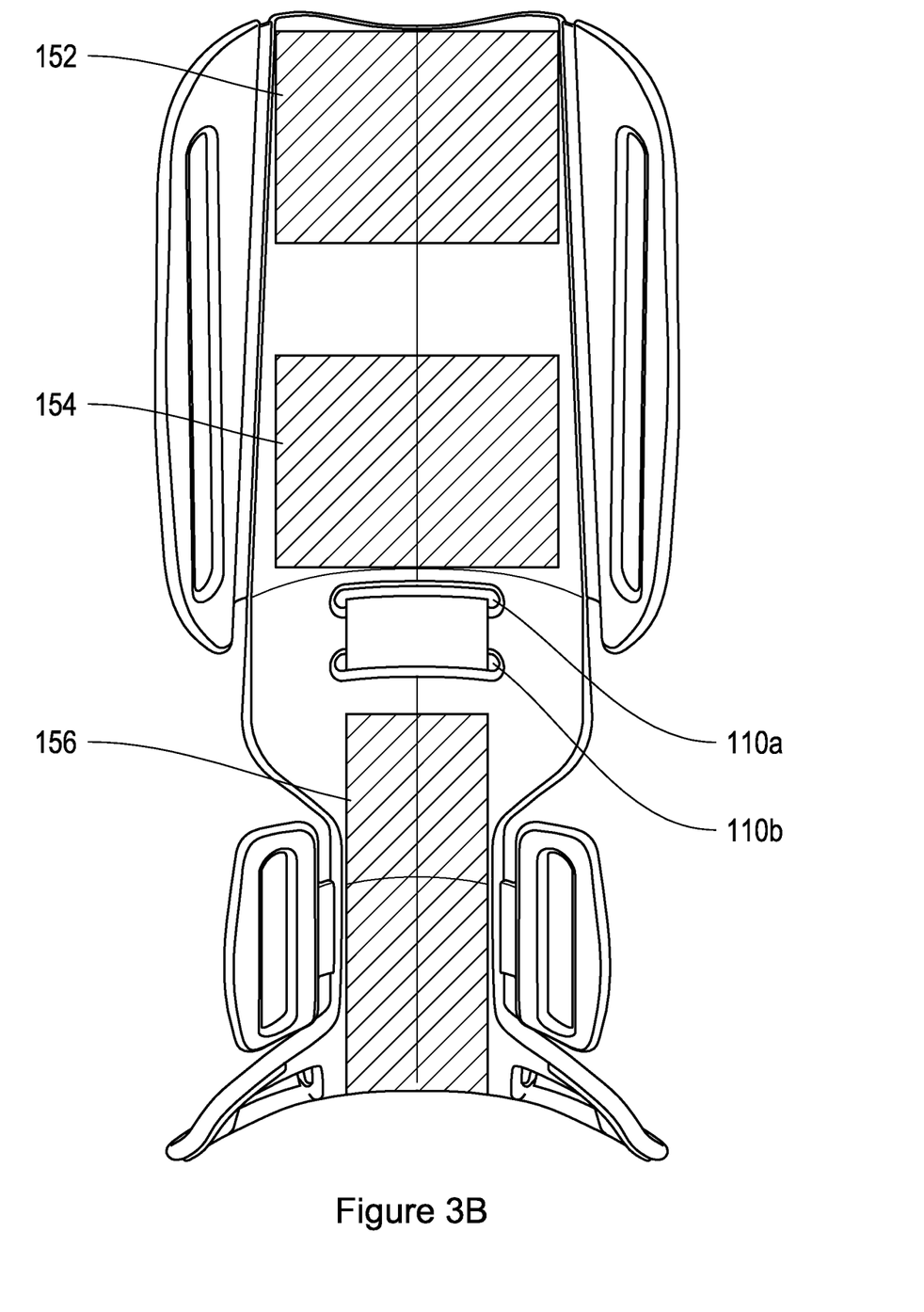

Also shown in FIGS. 3A and 3B, on the underside 102b of the frame 102, sections 150, 152, 154, 156, and 158 contain Velcro or other hook-and-loop attachment mechanisms and are included to connect the support pad 140 (which has complementary hook-and-loop materials on its surface) to the frame 102.

Figure 4A:
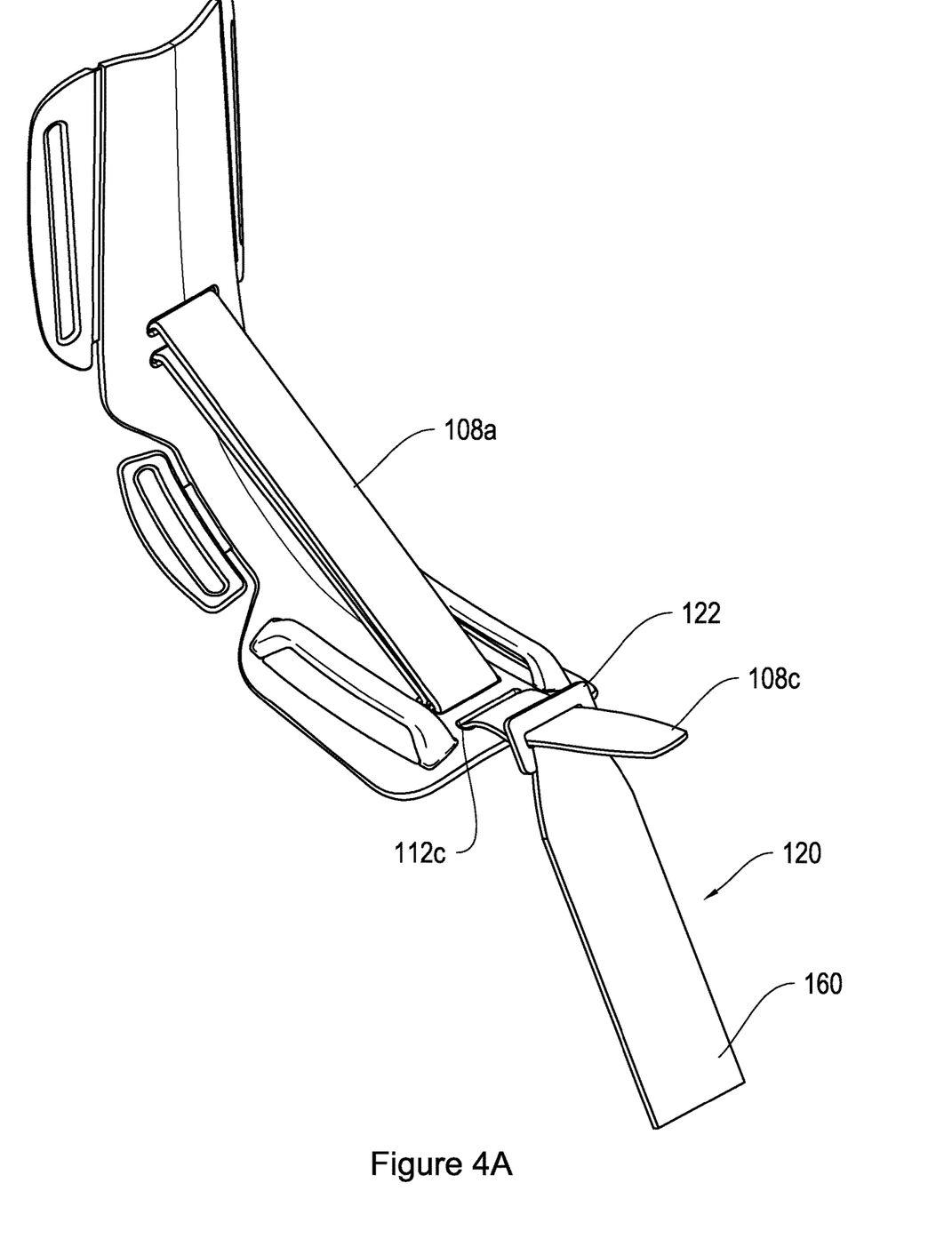
FIGS. 4A and 4B show additional implementations and embodiments of the frame and strapping systems of FIG. 1.
Figure 4B:
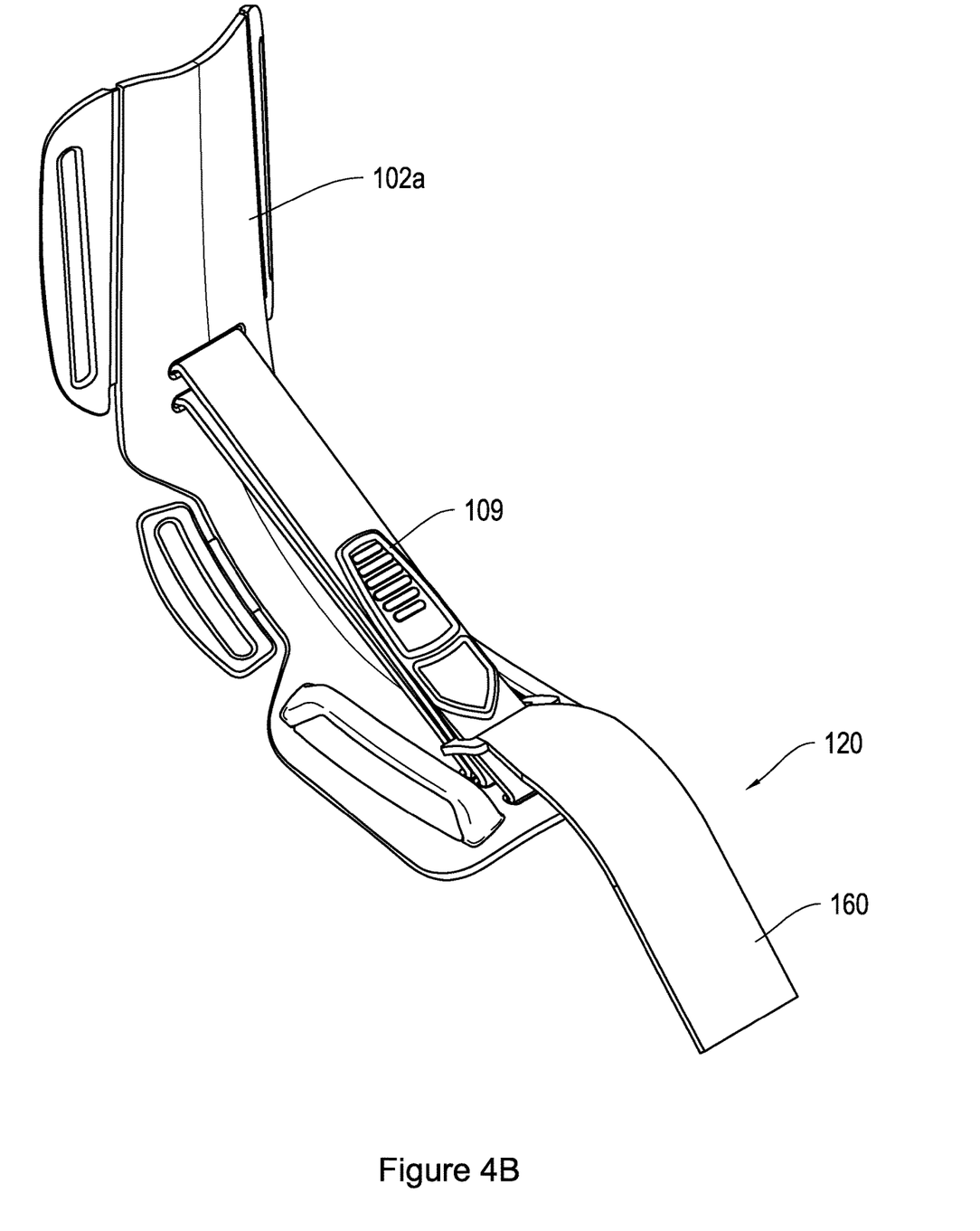

FIG. 4A further illustrates the forefoot strap 120. The strap 120 further lifts and supports the plantar fascia and the Achilles tendon. The strap 120 is configured with a D-ring 122 on an end thereof. The D-ring receives the distal section 108c of the strap 108. Thus, when the strap 108 is tightened by pulling the tab 109, the D-ring 122 is pulled tight against the splint by the strap 108, thereby anchoring the strap 120 to the strap 108. The distal end 160 of the strap 120 is anchored by Velcro or another attachment mechanism to the bottom side of the soft housing 114. When so anchored, the strap 120 extends from the bottom of the housing 114 across the front of the support pad 140, arcing over the patient's toes and anchoring to the top side of the soft housing 114.

Figure 5:
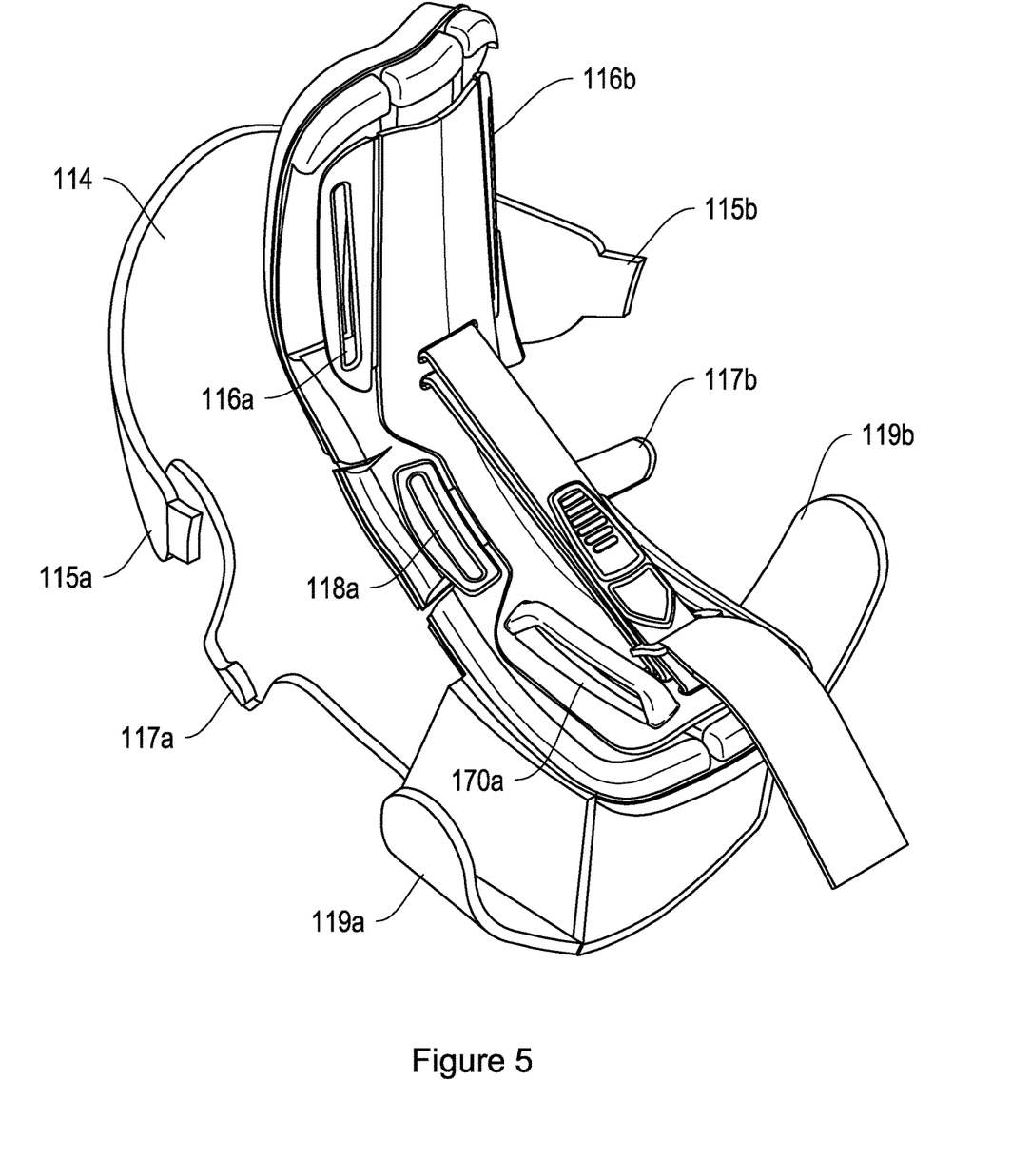
FIG. 5 shows an implementation of a dorsal night splint having a soft housing and brace componentry in an unattached configuration.

As noted above, the frame 102 is secured to the patient's leg by the flexible housing 114. The flexible housing 114 is preferably made of laminate material including 0.050" thick open-cell foam sandwiched between two layers of UBL (unbroken loop, a material that mates with hook material, e.g., from Velcro), the combination of which forms a soft, comfortable, breathable wrap that is easily attachable and detachable by the user. Other soft materials, such as Neoprene, may also be used. In use, the flexible housing 114 fits around the dorsal side of the patient's foot and lower leg. In the illustrated implementations, the housing 114 has attachment straps and hook-and-loop attachment surfaces for securing it to the frame 102. As shown more particularly in FIG. 5, the housing 114 includes the straps 115, 117, and 119, each strap having an analogous strap on the opposite side of the housing 114. As shown, the strap 115 has an end 115a and an end 115b. The end 115a fits within the slot 116a of the hinged flap 121. The strap end 115b fits within the corresponding slot 116b on the opposite side of the frame. Similarly, the strap 117a fits within the slot 118a of the hinged flap 125a, and the strap 117b fits within the slot 118b of the hinged flap 125b. The strap 119 fits within the slot 113, which has a raised ridge 170a that rises above the distal surface of the frame. The raised ridge 170a forms a tunnel through which the strap extension 119a can pass. A similar structure is used on the opposite side of the splint 100 for the receipt and tightening of the strap 119b. In use, the straps are inserted within their respective slots, from the under side 102b of the brace, and pulled up through the slots and folded and secured back upon themselves with the hook-and-loop connection. When fully assembled, the straps are fitted with respect to the frame as shown in FIG. 6.

Figure 7:
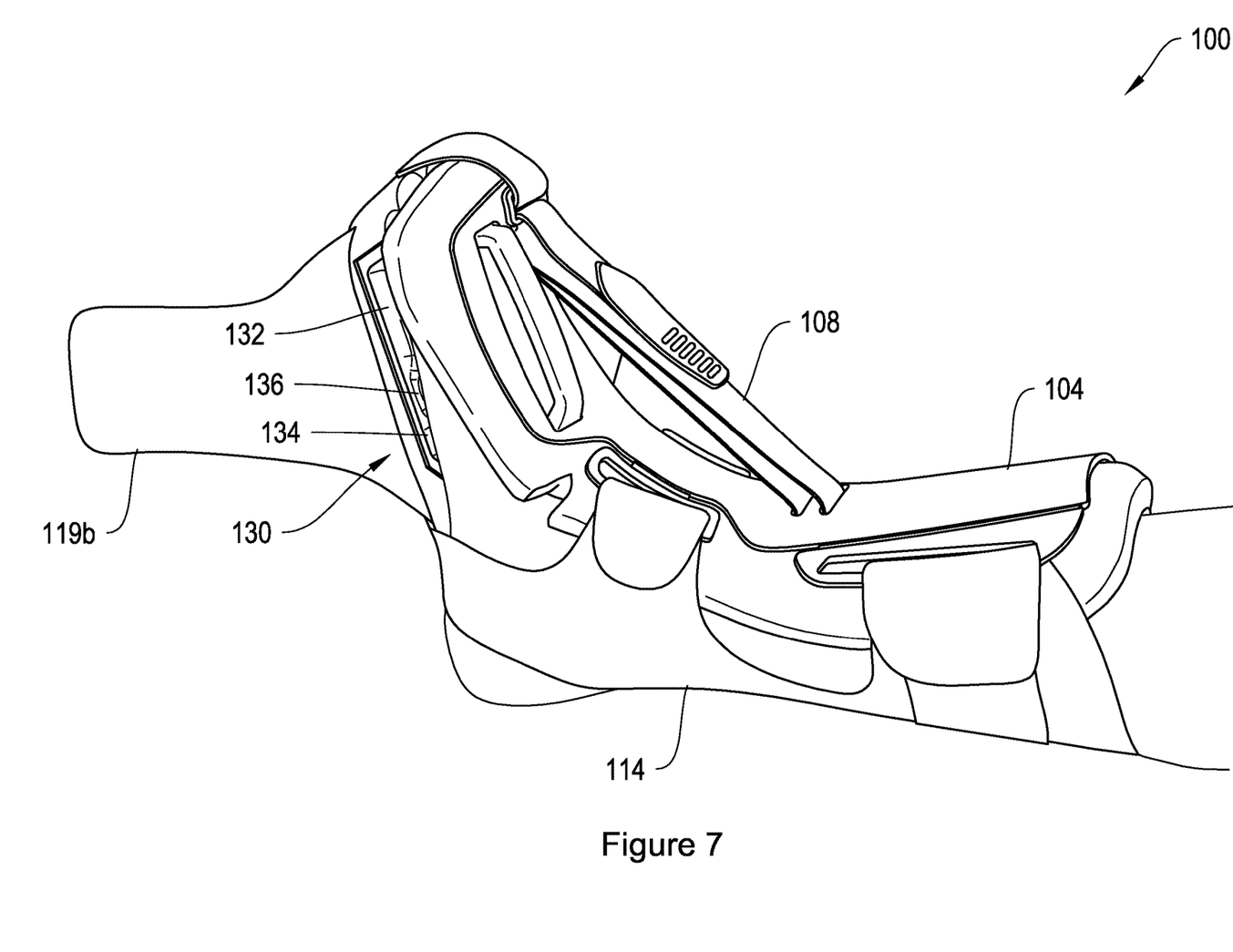
FIG. 7 depicts a support pad being used in a dorsal night splint.
Figure 8A:
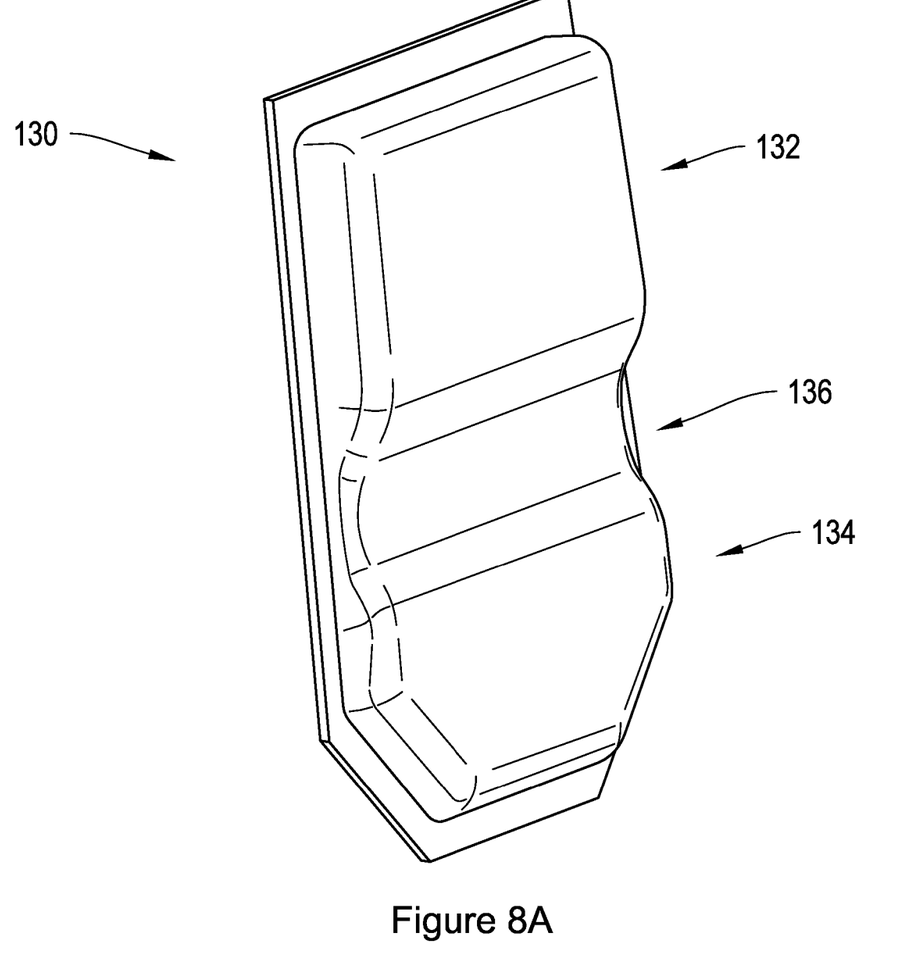
FIGS. 8A and 8B depict examples of the support pad of FIG. 7 in a dorsal night splint.
Figure 8B:
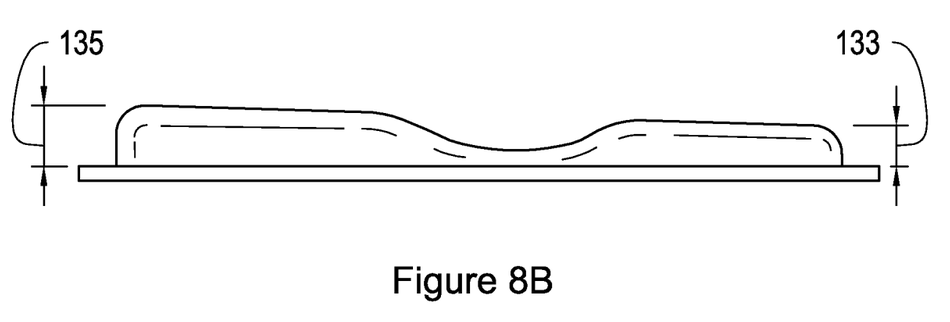

As shown in FIGS. 7 and 8A-8B, a forefoot pad 130 may also be used with the splint to help provide support for the patient's toes and the ball of the foot, further enhancing support for the plantar fascia. The foot pad 130 is placed underneath the foot and within the inner surface of the housing 114 and is releasably connected to the housing 114 by hook-and-loop material or another releasable attachment mechanism. As shown, the forefoot pad 130 includes an upper section 132, a lower section 134, and a trough 136. The upper section 132 is positioned to fit underneath the patient's toes, the lower section 134 is positioned to fit behind the ball of the patient's foot and support the upper arch, and the trough 136 is positioned to receive the ball of the foot. As shown in FIG. 8B, the upper section 132 has a thickness 135 that is greater than the thickness 133 of the lower section 134. The upper section 132 thus provides a distal lifting area, and is configured to lift the patient's toes higher than the upper arch would be lifted by the lower section 134. This distal lifting area works in concert with the toe strap 120, as well as the cross strap 108, to support the plantar fascia. The lower section 134 provides a proximal support area for the region of the patient's foot immediately behind the ball.

Figure 6:
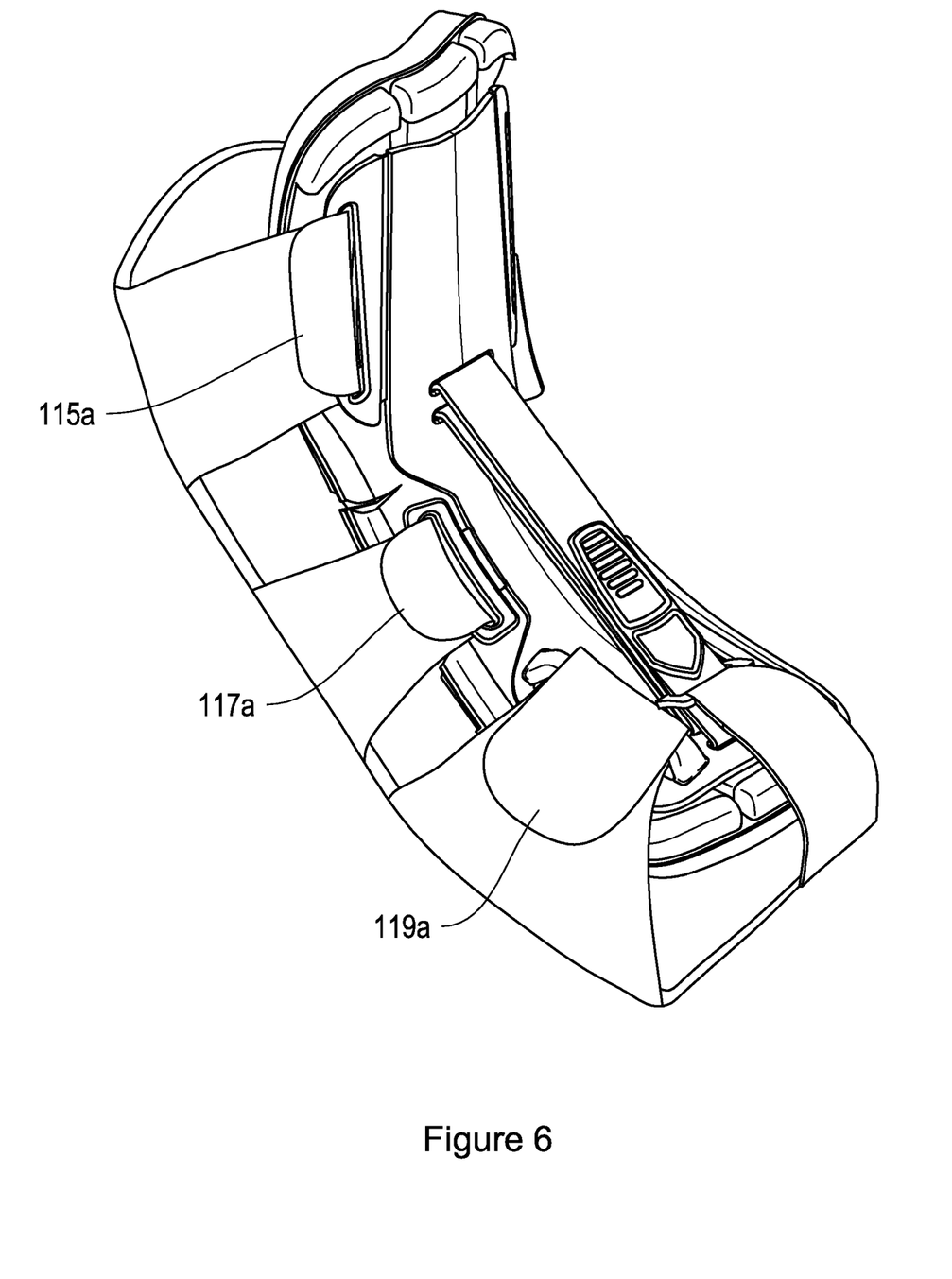
FIG. 6 depicts the dorsal night splint of FIG. 5 in an attached configuration.

FIG. 7 shows the assembled and attached splint structure of FIG. 6 having the strap 119 released and opened, and showing the insertion of the forefoot pad 130. As shown and described above, the forefoot pad 130 fits underneath the patient's foot, and supports the toes and ball of the foot as described above. After insertion of the pad, the strap 119 is then connected to the frame as described above to secure the frame (and the forefoot pad 130) to the patient.

It is to be understood that the forgoing description is merely illustrative. While several embodiments have been provided in the present disclosure, it should be understood that the disclosed systems, components, and methods may be embodied in many other specific forms, variations and modifications without departing from the scope of the present disclosure.

The disclosed features may be implemented in sub-combinations with one or more other features described herein, and the various features described or illustrated above may be combined or integrated in other systems or certain features may be omitted, or not implemented. A variety of orthopedic bracing products may be implemented based on the disclosure and still fall within the scope.

Examples of changes, substitutions, and alterations could be made by one of skill in the art without departing from the scope of the information disclosed herein. Certain particular aspects, advantages, and modifications are within the scope of the following claims. All references cited herein are incorporated by reference in their entirety and made part of this application.

What is claimed is:

1. A method of treating plantar fasciitis to an individual in need thereof, comprising:
    providing a splint for supporting a user's plantar fascia, said splint comprising:
        a flexible semi-rigid frame having a top side and an under side, the frame forming a proximal surface configured to extend vertically along a user's shin and upper ankle and a distal surface configured to extend along the top of the user's foot;
        a first receptacle in the proximal surface configured to engage a strap and a second receptacle in the distal surface configured to engage a strap;
        an adjustable inelastic tightening strap configured to engage the first and second receptacles; and
        a soft housing configured to attach the frame to the user's lower leg and fit under the user's foot;
    attaching said splint to a user's lower leg and foot;
    adjusting said tightening strap to pull a distal surface of said splint towards a proximal surface of said splint to stretch the user's plantar fascia.

2. The method of claim 1, wherein the frame includes a flap extending vertically along a side edge and attached to the edge by a hinge.

3. The method of claim 2, wherein said splint comprises first and second hinged flaps extending along lateral and medial edges, respectively, of the frame.

4. The method of claim 3, wherein the first receptacle is spaced between the first and second hinged flaps along the proximal surface.

5. The method of claim 3, wherein the first and second hinged flaps are co-molded and integral with the frame.

6. The method of claim 2, wherein the flap includes a slot configured to receive a portion of the soft housing, and wherein the slot bends along the hinge so as to conform to the user's leg.

7. The method of claim 1, wherein the tightening strap has a first end configured to anchor to one of the distal surface and the proximal surface of the frame and a second end, and wherein adjusting the tightening strap comprises pulling the second end to tighten the splint.

8. The method of claim 7, wherein the second end of the tightening strap is configured to extend from the second receptacle toward the user, at least when the splint is worn.

9. The method of claim 7, wherein pulling the second end draws the distal surface toward the proximal surface.

10. The method of claim 1, wherein said splint further comprises a forefoot support pad configured to be disposed between the user's toes and the soft housing.

11. The method of claim 10, wherein the forefoot support pad includes a distal lift area configured to fit under the user's toes and a proximal support area configured to fit behind the ball of the user's foot, wherein the distal lift area is thicker than the proximal support area.

12. The method of claim 1, wherein said splint further comprises an adjustable forefoot strap;
    and wherein said adjustable forefoot strap attaches to the soft housing and is configured to extend under the user's foot and across the front of the user's toes.

13. The method of claim 12, further comprising securing the forefoot strap to the splint by the inelastic tightening strap.

14. The method of claim 1, wherein said splint further comprises a bend between the proximal and distal surfaces and a space between the tightening strap and the bend.

15. A method of treating plantar fasciitis, comprising:
    providing a splint, said splint comprising
        a semi-rigid flexible frame having a proximal surface and a distal surface, and a bend that spans between the proximal and distal surfaces; wherein said semi-rigid flexible frame is configured to be applied along an anterior side of a user's foot and lower leg;
        a tightening strap anchored to said semi-rigid flexible frame and configured to allow the user to tighten the splint by pulling the tightening strap to draw the distal surface of the semi-rigid flexible frame toward the proximal surface of the semi-rigid flexible frame; and
        a soft housing attached to said semi-rigid flexible frame and configured to fit under the user's foot;
    applying the splint to a user's lower leg by wrapping said soft housing around a dorsal side of the foot to anchor said semi-rigid flexible frame to a user's leg;
    applying a proximal surface of the splint to a user's leg; and
    adjusting the splint by pulling said tightening strap to draw the distal surface of the semi-rigid flexible frame towards the proximal surface of the semi-rigid flexible frame-after said splint is applied to the user's leg;
    wherein said adjusting allows the user to achieve tailored flexion as the splint stretches the user's plantar fascia.

16. The method of claim 15, wherein the tightening strap has a first end configured to anchor to one of the distal surface and the proximal surface of the semi-rigid flexible frame and a second end, the splint being configured such that pulling the second end tightens the splint.

17. The method of claim 16, wherein the tightening strap forms a pulley having a first section, a second section, and a fold between the first and second sections.

* * * * *